(12) United States Patent
Golz-Berner et al.

(10) Patent No.: US 6,534,046 B1
(45) Date of Patent: Mar. 18, 2003

(54) PLANT-BASED ANTI-PERSPIRATION COSMETIC

(75) Inventors: Karin Golz-Berner, Monaco (MC); Leonhard Zastrow, Monaco (MC); Virginie Fajon, Nice (FR)

(73) Assignee: Coty B.V. (NL)

( * ) Notice: Subject to any disclaimer, the term of this patent is extended or adjusted under 35 U.S.C. 154(b) by 0 days.

(21) Appl. No.: 10/202,696

(22) Filed: Jul. 25, 2002

(30) Foreign Application Priority Data

Aug. 1, 2001 (DE) .......................................... 101 37 730

(51) Int. Cl.$^7$ ............................. A61K 7/32; A61K 31/20
(52) U.S. Cl. ............................................ 424/65; 514/558
(58) Field of Search ............................. 424/65; 514/558

*Primary Examiner*—Alton Pryor
(74) *Attorney, Agent, or Firm*—Pendorf & Cutliff

(57) ABSTRACT

The invention refers to an anti-sweat cosmetic which is suitable for use on the whole body and whose ingredients are almost entirely plant-based. The anti-perspiration cosmetic contains 0.01 to 5% by weight of a mixture of the extract of the overground plant parts of *Equisetum arvense* and the essential oil of *Salvia officinalis*; 0.01 to 5% by weight of a mixture of the extracts of *Hamamelis virginia* and *Quercus infectoria*; 0.5 to 15% by weight of pulverized bamboo wood (Bamboo Powder) the particle size of which is 15 μm or smaller; ad 100% by weight cosmetic auxiliaries, carrier substances or further active agents or mixtures thereof.

8 Claims, No Drawings

PLANT-BASED ANTI-PERSPIRATION COSMETIC

BACKGROUND OF THE INVENTION

1. Field of the Invention

The invention refers to an anti-sweat cosmetic which is suitable for use on the whole body and whose ingredients are almost entirely plant-based.

2. Description of the Related Art

Deodorizing cosmetics are used to at least temporarily conceal or absorb the odours produced by sweating of the human body. They are usually marketed in the form of solutions, powders or sticks.

EP 1002521 discloses a cosmetic containing sage extracts. DE-199 62 881 describes an anti-perspiration composition consisting of an anti-sweat agent, such as salts of Al, Zr or Zn, combined with a particulate, water-soluble polysaccharide and a wax. DE 4304284 discloses a deodorant based on lavender oil and horsetail extract.

SUMMARY OF THE INVENTION

The object of the invention is to provide a cosmetic containing plant-based active agents which absorbs the sweat given off by the body and temporarily conceals odours.

According to the invention, the anti-perspiration cosmetic consists of a mixture of 0.01 to 5% by weight of a mixture of the extract of the overground plant parts of *Equisetum arvense* and the essential oil of *Salvia officinalis;* 0.01 to 5% by weight of a mixture of the extracts of *Hamamelis virginia* and *Quercus infectoria;* 0.5 to 15% by weight of pulverized, bamboo wood (Bamboo Powder) the particle size of which is 15 μm or smaller; ad 100% by weight cosmetic auxiliaries, carrier substances or further active agents or mixtures thereof; all % by weight in relation to the cosmetic.

The extract of *Equisetum arvense* is obtained using propylene glycol at temperatures ranging from 20 to 40° C. The ratio of Equisetum to Salvia can be in the range of 20:80 to 80:20. Preferably, the mixture is present in the form of an aqueous solution in propylene glycol.

It is advantageous to add 0.01 to 2% by weight of a mixture of *Equisetum arvense* and *Salvia officinalis,* Equisetum also being able to be added as a separate ingredient.

The extract of *Hamamelis virginia* and *Quercus infectoria* is an extract obtained from the overground parts of the plants using propylene glycol at temperatures ranging from 20 to 40° C. The ratio of both constituents can be in the range of 5:95 to 95:5. Preferably, the mixture is present in the form of an aqueous solution in propylene glycol. It can additionally contain amino acids, such as Glycine, Arginine, Leucine and mixtures thereof.

Further, 0.01 to 2% by weight of an active agent can be contained selected from the group consisting of the essential oils of eucalyptus, lemon, myrrh, sandal and mixtures thereof.

Preferably, the Bamboo Powder used consists of pulverized medulla of *Bambusa arundinaceae* having a preferred medium particle size of about 5 μm and approximately 60% of the particles being in the range of 2–6 μm. This particular bamboo species is native to some Indian mountain woods and is particularly suitable for, absorbing sebum and texturizing cosmetic products. The Bamboo Powder preferably makes up 4–12% by weight. A particularly preferred product is Greensil of Greentech, St. Beauzire, France.

As a further active ingredient, the preparation can advantageously contain kaolin according to WO96/17588 which is modified with spherical $TiO_2$ or $SiO_2$ particles of a particle size of <5 μm, wherein the spherical particles have a proportion in the kaolin mixture of 0.5 to 10 wt. %. This imparts to the preparation a very soft skin feel and, additionally, an anti-inflammatory action.

The modified kaolin and can have a proportion of 0.1 to 15 wt. %, relative to the total weight of the product.

In one embodiment of the invention, a powder consisting of Methyl Methacrylate/Ethylen Glycol Bismethacrylate copolymer can be added, which powder has an average particle size of about 8 μm and is present in the form of macro-porous globules. The PMMA powder content can be in the range of 0.5 to 10% by weight.

The inventive preparation contains also cosmetic auxiliary and carrier substances as they are used conventionally in such compositions, for example, water, preservatives, colorings, pigments, polyols, such as Glycerine and Propylene Glycol and Butylene Glycol, esters or ethers, electrolytes, polar and non-polar oils, polymers, copolymers, emulsifiers, waxes, gels, stabilizers, amines, such as Triethanolamine, or mixtures thereof. The oils added should make up <5% by weight.

Further additives or active agents in the cosmetic compositions can be vitamins, e.g. Vitamin A or derivatives thereof; organic sunscreens, such as e.g. Octyl Methoxycinnamate; Methyl Gluceth 10 or Methyl Gluceth 20.

In another embodiment, an active agent contained in the cosmetic can be 0.01 to 2% by weight of Zinc Ricinoleate, which can also be added in a solubilized form together with Propylene Glycol, Triethanolamine and Lactic Acid.

Pigments, pigment mixtures or powders with a pigment-like effect, also including those with a pearl-gloss effect, may include, for example, iron oxides, aluminum silicates such as ochre, titanium (di)oxide, mica, kaolin, manganese containing clays such as umber and red bole, calcium carbonate, French chalk, mica-titanium oxide, mica-titanium oxide-iron oxide, bismuth oxychloride, nylon beads, ceramic beads, expanded and non-expanded synthetic polymer powders, powdery natural organic compounds such as milled solid algae, milled plant parts, encapsulated and non-encapsulated cereal starches and mica-titanium oxide-organic dye.

Suitable esters or ethers are, for example, (INCI designations): Dipentaerythrityl Hexacaprylate/Hexacaprate/Tridecyl Trimellitate/Tridecyl Stearate/Neopentyl Glycol Dicaprylate Dicaprate, Propylene Glycol Dioctanoate 5, Propylene Glycol Dicaprylate 2,30 Dicaprate, Tridecyl Stearate/neopentyl glycol dicaprylate dicaprate/tridecyl trimellitate, Neopentyl Glycol Dioctanoate, Isopropyl Myristate, Diisopropyl Dimer Dilinoleate, Trimethylpropane Triisostearate, Myristyl Ether, Stearyl Ether, Cetearyl Octanoate, Butyl Ether, Dicaprylyl Ether, PPG1-PEG9 Lauroyl Glycol Ether, PPG15 Stearyl Ether, PPG14 Butyl Ether, Fomblin HC25.

Cosmetic oils used in small amounts can be vegetable oils, such as Calendula Oil, Jojoba Oil, Avocado Oil, Macadamia Nut Oil, Castor Oil, Wheatgerm Oil, Grapeseed Oil, Kukui Nut Oil, Thistle Oil, Evening Primrose Oil, Safflower Oil or a mixture of several thereof. Mineral oils can also be used.

Cosmetic gels can also be added. Suitable gel-forming agents include Carbomer, xanthan gum, carrageenan, acacia gum, guar Gum, Agar-Agar, alginates and tyloses, carboxymethyl cellulose, hydroxyethyl cellulose, quaternized cellulose, quaternized guar, certain polyacrylates, polyvinyl alcohol, polyvinylpyrrolidone, montmorillonite. Plant-based gels are preferred.

It is moreover advantageous to add to the compositions according to the invention corresponding water and/or oil soluble UVA or UVB filters or both. Advantageous oil-soluble UVB filters include 4-amino benzoic acid derivatives- such as 4-(dimethylamino)-benzoic acid-(2-ethylhexyl) ester; esters of cinnamic acid such as 4-methoxy cinnamic acid (2-ethylhexyl) ester, benzophenone derivatives such as 2-hydroxy-4-methoxy benzophenone; 3-benzylidene camphor derivatives such as 3-benzylidene camphor.

Preferred oil-soluble UV filters are Benzophenone-3, Butyl-Methoxybenzoylmethane, Octyl Methoxycinnamate, Octyl Salicylate, 4-Methylbenzylidene Camphor, Homosalate and Octyl Dimethyl PABA.

Water-soluble UVB filters are, for example, sulfonic acid derivatives of benzophenone or of 3-benzylidene camphor or salts, such as Na or K salts, of 2-phenyl benzimidazole-5-sulfonic acid.

UVA filters include dibenzoyl methane derivatives such as 1-phenyl-4-(4'-isopropanol phenyl) propane-1,3-dione.

Preferred as sunscreen filters are inorganic pigments on the basis of metal oxides, such as $TiO_2$, $SiO_2$, ZnO, $Fe_2O_3$, $ZrO_2$, MnO, $Al_2O_3$, which cane also be used in mixtures thereof.

Especially preferred as inorganic pigments are agglomerate substrates of $TiO_2$ and/or ZnO according to WO99/06012 which have a contents of spherical and porous $SiO_2$ particles, wherein the $SiO_2$ particles have a particle size in the range of 0.05 $\mu$m to 1.5 $\mu$m, and, in addition to the $SiO_2$ particles, other inorganic particle-like substances with spherical structure are present, wherein the spherical $SiO_2$ particles form defined agglomerates with the other inorganic substances with a particle size in the range of 0.06 $\mu$m to 5 $\mu$m.

The cosmetic according to the invention can have the form of a cream, a powder, a make-up, a foundation, a sprayable powder. Emulsions of the said cosmetic do not contain any film-forming agent and in general should be very dry.

The cosmetic absorbs sweat to a high degree thus constituting an outstanding class of cosmetics since it is not primarily intended to directly conceal odours, but to actually absorb sweat to a high degree by means of plant-based active agents alone. In this way, irritations of the skin are largely avoided.

The invention will hereinafter be explained in more detail by way of examples. All quantities are in % by weight if not indicated otherwise.

EXAMPLE 1

Body and Face Cream

| Phase A | |
|---|---|
| Glyceryl Stearate | 5 |
| PEG100 Stearate | 1 |
| Vaseline | 1.5 |
| Paraffin | 0.5 |
| Phase B | |
| Water | ad 100 |
| Glycerine | 5 |
| Bamboo Powder (*Bambusa arundinaceae*) | 10 |
| Phase C | |
| Extract of *Equisetum arvense* | 0.01 |
| Extract of *Hamamelis virginia* and *Quercus infectoria* | 3.2 |
| Eucalyptus Oil | 0.2 |
| Mixture of *Equisetum arvense* and *Salvia officinalis* | 0.3 |
| Preservative | 0.2 |

Phases A and B are prepared separately by mixing the respective ingredients and heated up to a temperature of 70–80° C. Both phases are combined while stirring, homogenized using a homogenizer and cooled down to approximately 40° C. Phase C is prepared separately by mixing the individual ingredients and added into the homogeneous mixture at 30–35° C. while stirring. In a variant of this example, 0.5% by weight of Zinc Ricinoleate was added to Phase C.

EXAMPLE 2

Hand and Foot Cream

| Phase A | |
|---|---|
| Cetyl Alcohol | 1 |
| Cetearyl Alcohol | 1.5 |
| PEG20 Stearate | 2.5 |
| Cetearyl Octanoate | 1 |
| Phase B | |
| Water | ad 100 |
| Propylene Glycol | 2 |
| Glycerine | 3 |
| Bamboo Powder | 5 |
| Phase C | |
| Zinc Ricinoleate | 0.02 |
| Extract of *Equisetum arvense* | 3.5 |
| Extract of *Hamamelis virginia* and *Quercus infectoria* | 2.0 |
| Lemon Oil | 0.5 |
| Mixture of *Equisetum arvense* and *Salvia officinalis* | 0.3 |
| Preservative | 0.2 |

Processing was done as in Example 1.

EXAMPLE 3

Anti-perspiration Powder

| | |
|---|---|
| Kaolin (modified according to WO96/17588) | 15 |
| Talc | ad 100 |
| Zinc Ricinoleate | 2 |
| Extract of *Equisetum arvense* | 5 |
| Extract of *Hamamelis virginia* and *Quercus infectoria* | 5 |
| Sandal Oil | 1 |
| Bamboo Powder | 10 |
| Mixture of *Equisetum arvense* and *Salvia officinalis* | 2 |

The ingredients are mixed with one another in the order indicated above.

EXAMPLE 4

Comparative Example 1

A study was carried out in which the Trans-Epidermal Water Loss (TEWL) of three skin areas located on the shoulder blades and the breastbone of 15 test persons (male and female) between 14 and 19 years of age was measured.

The tests were carried out as follows:

A) without treatment

B) cream according to Example 1

Power Trail on the ergometer, 0 to 1500 watts during max. 60 minutes; measuring heads fixed in a way that the TEWL can be measured and an ECG recorded; bioclimate-controlled room; permissible pulse limited to 160 beats per minute.

TABLE I

| Minutes/Watts | Water Loss (WE) in g/m² | |
|---|---|---|
| | A | B |
| 5/250 | 21 | 18 |
| 10/250 | 45 | 21 |
| 15/250 | 63 | 32 |
| 20/500 | 82 | 38 |
| 25/500 | 94 | 48 |
| 30/750 | 105 | 75 |
| 40/1000 | 112 | 91 |
| 50/1250 | 123 | 97 |
| 60/1500 | 130 | 105 |

EXAMPLE 5

Comparative Example 2

A physiological Power Trail was carried out, the number of test persons being the same as in Example 4. Measuring heads fixed in a way that the TEWL can be measured and an ECG recorded; bioclimate-controlled room; permissible pulse limited to 160 beats per minute.

At the beginning of the test was a 15 minutes' Power Trail at a constant load of 500 W. This was followed by a 5 minutes' break during which the skin was dried and the cream according to Example 1 applied. Then another 15 minutes' Power Trail at a constant load of 500 W followed.

TABLE II

| Minutes/Watts | Water Loss (WE) in g/m² | |
|---|---|---|
| | A | B |
| 5/250 | 28 | 28 |
| 10/500 | 53 | 53 |
| 15/500 | 65 | 66 |
| BREAK 5 min. | | |
| 25/500 | 70 | 49 |
| 30/500 | 101 | 56 |
| 35/500 | 116 | 78 |

Comparative Examples 4 and 5 show that the application of the cream B brings about a clear effect as regards the reduction of the Epidermal Water Loss, which in some cases decreases by more than 100%.

EXAMPLE 6

Comparative Example 3

A test in which several groups of hip hop dancers aged 16.6 years on average danced for 13 to 30 minutes at a room temperature of 33° C. and a relative air humidity of 65% also showed a clear reduction of the Epidermal Water Loss (g/m²) by 20–40% compared to dancers who had not been treated.

What is claimed is:

1. A plant-based anti-perspiration cosmetic which comprises 0.01 to 5% by weight of a mixture of the extract of the overground plant parts of *Equisetum arvense* and the essential oil of *Salvia officinalis*;

0.01 to 5% by weight of a mixture of the extracts of *Hamamelis virginia* and *Quercus infectoria*;

0.5 to 15% by weight of pulverized bamboo wood the particle size of which is 15 μm or smaller;

and balance cosmetic auxiliaries, carrier substances or further active agents or mixtures thereof, all % by weight in relation to the cosmetic.

2. A cosmetic according to claim 1 wherein the said cosmetic contains 0.01 to 2% by weight of Zinc Ricinoleate as a further active agent.

3. A cosmetic according to claim 1 wherein the said cosmetic contains Kaolin as a further active agent, which Kaolin has been modified with spherical $TiO_2$ or $SiO_2$ particles the particle size of which is <5 μm, the spherical particles making up 0.5 to 10% by weight of the kaolin mixture.

4. A cosmetic according to claim 1 wherein the said cosmetic contains 0.01 to 2% by weight of the mixture of *Equisetum arvense* and *Salvia officinalis*.

5. A cosmetic according to claim 1 wherein the said cosmetic contains 0.01 to 2% by weight of the extract of *Equisetum arvense*.

6. A cosmetic according to claim 1 wherein the said cosmetic contains 0.01 to 2% by weight of an active agent selected from the group consisting of the oils of eucalyptus, lemon, myrrh, sandal and mixtures thereof.

7. A method for reduction of moisture loss from the epidermis, comprising applying to the epidermis a composition comprising 0.01 to 5% by weight of a mixture of the extract of the overground plant parts of *Equisetum arvense* and the essential oil of *Salvia officinalis*;

0.01 to 5% by weight of a mixture of the extracts of *Hamamelis virginia* and *Quercus infectoria*;

0.5 to 15% by weight of pulverized bamboo wood the particle size of which is 15 μm or smaller;

and balance cosmetic auxiliaries, carrier substances or further active agents or mixtures thereof.

8. A composition for prevention of moisture loss from the epidermis, comprising 0.01 to 5% by weight of a mixture of the extract of the overground plant parts of *Equisetum arvense* and the essential oil of *Salvia officinalis*;

0.01 to 5% by weight of the extracts of *Hamamelis Virginia* and *Quercus infectoria*;

0.5 to 15% by weight of pulverized bamboo wood the particle size of which is 15 μm or smaller;

and balance cosmetic auxiliaries, carrier substances or further active agents or mixtures thereof.

* * * * *